United States Patent [19]
Kuntz et al.

[11] 3,933,753
[45] Jan. 20, 1976

[54] ALKENYLAROMATIC POLYMERS WITH α-KETOALHYDIC GROUPS

[75] Inventors: Emile Kuntz; Jean Pierre Quentin, both of Rhone, France

[73] Assignee: Rhone-Poulenc S.A., Paris, France

[22] Filed: Feb. 1, 1973

[21] Appl. No.: 328,591

[30] Foreign Application Priority Data
Feb. 4, 1972  France .............................. 72.03804

[52] U.S. Cl. ............ 260/63 R; 210/24; 260/63 UY; 260/66; 260/67 UA; 260/79; 260/79.3 M; 260/83.7; 260/85.1; 260/87.3; 260/88.1 P; 260/88.1 R; 260/88.1 PN; 260/88.1 PC; 260/88.2 C
[51] Int. Cl.² ................... C08G 2/38; C08G 10/06
[58] Field of Search...260/63 UY, 63 R, 79, 79.3 M, 260/66, 67 UA, 83.7, 85.1, 87.3, 88.1 R, 88.1 P, 88.1 PN, 88.1 PC, 88.2 C

[56] References Cited
UNITED STATES PATENTS

| | | | |
|---|---|---|---|
| 2,437,980 | 3/1948 | Seymour et al. | 260/63 |
| 2,579,759 | 12/1951 | Russell | 260/47 |
| 3,056,765 | 10/1962 | Cowherd et al. | 260/79.3 |
| 3,388,111 | 6/1968 | Allen et al. | 260/93.5 |
| 3,694,408 | 9/1972 | Hynds et al. | 260/47 |

*Primary Examiner*—Lester L. Lee
*Attorney, Agent, or Firm*—Stevens, Davis, Miller & Mosher

[57] ABSTRACT

An alkenylaromatic polymer is provided derived from 50 to 100 mol % of at least one monomer of the general formula:

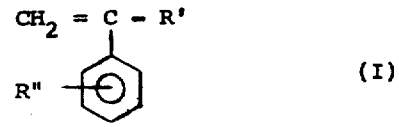

in which R' represents a hydrogen atom or a methyl radical and R'' represents a hydrogen atom or a methyl or ethyl radical, and 0 to 50 mol % of a nonaromatic ethylenically unsaturated monomer, optionally crosslinked by 0.1 to 30 mol %, relative to the monomer of formula (I), of a polyvinyl monomer, 0.01 to 1 α-ketoaldehyde group of the formula $$- CO - CHO \qquad (II)$$

being present per aromatic ring in the polymer. These polymers find particular utility in extracting sulphur and nitrogen-containing compounds from solutions containing them, especially urea from solutions resulting from the dialysis or ultrafiltration of human blood.

18 Claims, No Drawings

ALKENYLAROMATIC POLYMERS WITH α-KETOALHYDIC GROUPS

The present invention relates to alkenylaromatic polymers containing α-ketoaldehydic functional groups.

According to the present invention there is provided an alkenylaromatic polymer derived from 50 to 100 mols per 100 mols of one or more monomers of the general formula:

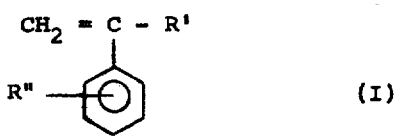

in which R' represents a hydrogen atom or a methyl radical and R" represents a hydrogen atom or a methyl or ethyl radical, and up to 50 mol per cent of a non-aromatic ethylenically unsaturated monomer, optionally crosslinked by 0.1 to 30 mol %, relative to the monomer of formula (I), of a polyvinyl monomer, and which contains 0.01 to 1 α-ketoaldehyde group of the formula:

per aromatic ring present in the polymer.

As examples of monomers of formula (I) there may be mentioned styrene, α-methylstyrene, m-vinyltoluene and m-ethylstyrene. Amongst the ethylenic monomers which can optionally be combined with the alkenylaromatic monomers there may be mentioned ethylene, propylene, butadiene and isoprene. Compounds such as m-divinylbenzene, p-divinylbenzene and mixtures thereof, diisopropenylbenzenes, vinyltoluenes, 1,3,5-trivinylbenzene, 1,2,4,-trivinylbenzene, divinylxylenes, allyl phthalate and triallyl cyanurate can be used as crosslinking monomers.

The present invention also provides a process for the preparation of the alkenylaromatic polymers which comprises reacting dimethylsulphoxide with an alkenylaromatic polymer derived from 50 to 100 mol % of one or more monomers of formula (I) and up to 50 mol % of a non-aromatic ethylenic monomer, optionally crosslinked by 0.1 to 30 mol %, relative to the monomer of formula (I), of a polyvinyl monomer, and containing 0.01 to 1 haloacetyl group of the general formula:

in which X represents a halogen atom, especially chlorine or bromine, per aromatic ring present in the polymer.

The polymers and copolymers which may or may not be crosslinked and which contain α-ketoaldehyde groups will hereafter be referred to as "polyalkenylarylglyoxal", and the polymers and copolymers which contain halogenoacetyl groups used to prepare these will hereafter be denoted by "polyalkenylphenacyl halide".

The reaction conditions vary greatly depending on the nature of the polyalkenylphenacyl halide employed and, especially, on whether it is a polymer which is soluble or insoluble in the sulphoxide or in another organic solvent.

The temperature of the reaction can generally vary between 0° and 200°C, preferably between 20° and 150°C. The amount of sulphoxide employed, expressed in mols of sulphoxide per halogenoacetyl group present in the starting polymer, can vary within wide limits. Thus an amount of sulphoxide close to the stoichiometric requirements of the reaction or a deficiency or an excess can be used; for example, it is possible to employ 0.1 to 2 mols of sulphoxide per halogenoacetyl group. In this case, the reaction is suitably carried out in a solvent for the polymer which is inert under the reaction conditions, when the polymer is soluble, or in an inert dispersing agent, preferably having a swelling action, when the polymer is insoluble, for example for polymers crosslinked by a polyvinyl monomer. For practical reasons, it is however preferable to use the sulphoxide as the reaction medium, since the halogenated polymers undergoing reaction are generally soluble in or swelled by, the sulphoxide. Under these conditions, the sulphoxide is used in great excess relative to the amount theoretically required. The degree of conversion of the halogenoacetyl groups present in the starting polymer can be controlled by the amount of sulphoxide employed and, where necessary, by the duration of the reaction which does, of course, vary depending on the nature of the starting product and on the temperature conditions. In this way, it is possible to introduce a varying number of α-ketoaldehyde groups in the final polymers. The optimum conditions for the reaction in each particular case can be determined easily by means of simple experiments.

When the reaction is carried out in the presence of an inert solvent or diluent, organic compounds which are liquid under the reaction conditions such as aliphatic hydrocarbons such as pentane and hexane, cycloaliphatic hydrocarbons such as cyclohexane, aromatic hydrocarbons such as benzene and toluene and ethers such as diethyl ether are suitable.

The polyalkenylphenacyl halides used as the starting material can be obtained by various known processes. They can, for example, be prepared by halogenation of an alkenylaromatic polymer containing 0.01 to 1 acetyl group per aromatic group, hereafter referred to as "polyalkenylacetophenone", by means of a halogen in the presence of a hydracid. The polyalkenylacetophenone can be dissolved or suspended in a suitable solvent such as a lower aliphatic carboxylic acid such as acetic acid or chlorinated solvent such as chloroform, containing the hydracid. Such a process has been described by W. O. KENYON et al., J. Polym. Sci., 32, 83–85 (1958) for brominated poly-p-vinylacetophenone and by R. BECKERBAUER et al., J. Polym. Sci., A-2, 823–834 (1964) for brominating a styrene/p-vinylacetophenone copolymer. The polyalkenylacetophenones, in their turn, can be obtained in known manner by polymerisation or copolymerisation of an alkenylacetophenone with at most 50 mol % of an ethylenic monomer. A portion of the alkenylacetophenone can also be replaced by an alkenylaromatic monomer of formula (I) such as styrene or α-methylstyrene and/or a polyvinyl monomer in the proportions indicated above. In every case, the amount of alkenylaromatic monomer should be calculated so that the number of acetyl groups relative to the number of aromatic groups remains within the range 0.01 to 1. The polyalkenylacetophenones can also be prepared in known manner by acetylation of a polymer, or a copolymer (optionally crosslinked) of at least 50 mol %, of one or more monomers of formula (I) and at most 50 mol % of a non-aromatic ethylenic monomer such as those already mentioned, using an acetylating agent such as acetic anhydride, ketene or an acetyl halide, for example the bromide or chloride, in the presence of the usual catalysts and solvents for Friedel-Crafts reactions, aluminium chloride is preferably used as the catalyst. Carbon disulphide, carbon tetrachloride, nitromethane, chloronitromethane, dichlorobenzene, monochlorobenzene or nitrobenzene may be mentioned as suitable solvents. The last solvent is especially suitable for acetylating crosslinked alkenylaromatic polymers, on which it has a swelling action. Acetylation of alkenylaromatic polymers and especially of polystyrene has been described by W. O. KENYON et al., loc. cit.; R. BECKERBAUER et al., loc. cit.; J. A. BLANCHETTE et al., J. Org. Chem., 23 1117–22 (1958) and in U.S. Pat. Nos. 2,713,570 and 2,962,485. When the alkenylaromatic polymer is insoluble in a solvent, acetylation can still be carried out in accordance with the processes described for example, in U.S. Pat. Nos. 3,299,025 and 3,304,294, in accordance with which a gaseous stream of the acetylating agent, and optionally of the catalyst, is passed through the polymer in powder form, optionally containing the catalyst.

In accordance with another process, the polyalkenylphenacyl halide are prepared by direct halogenoacetylation of an alkenylaromatic polymer as defined above, in known manner. Thus the chloroacetylation and bromoacetylation of polystyrene have been described by W. O. KENYON, loc. cit., and in U.S. Pat. No. 2,713,570.

With the non-crosslinked polymers, the molecular weight of the polyalkenylphenacyl halides, which determines that the final polymers, can vary within wide limits because it is not critical. Thus use can generally be made of polymers of average molecular weight between 1,000 and 1,000,000.

When the oxidation reaction of the polyalkenylphenacyl halide is not carried out in solution, and especially when crosslinked polymers are involved, the polymer can be employed in various physical forms such as finely divided powders, cylindrical granules and balls. Whatever their form, the polymer particles can have been treated in known manner to increase their porosity and, consequently, the surface area of contact with the oxidising agent. Thus granules or balls of expanded polymer can be used.

Without limiting the invention in any way to a particular mechanism, it is believed that the reaction can be represented by the following equation:

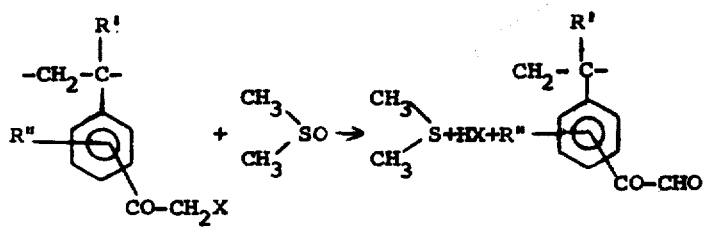

When the polyalkenylphenacyl halide contains less than 1 halogenoacetyl group per aromatic group, the remaining aryl groups can be unsubstituted or substituted wholly or partly by residual acetyl groups, depending on the process and the reaction conditions. Likewise, it is possible for the polyalkenylarylglyoxals obtained by oxidation to contain aromatic groups which are unsubstituted by acetyl or halogenoacetyl groups or which are substituted wholly or partly by acetyl and/or halogenoacetyl groups, in an amount of at most one of these groups per aromatic ring.

In short, depending on the process by which they are obtained, the polyalkenylphenacyl halides can consist wholly, in the case of the alkenylaromatic part, of units of the formula:

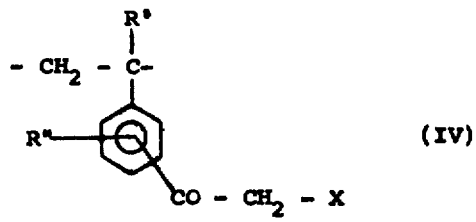

or can contain units of the formulae:

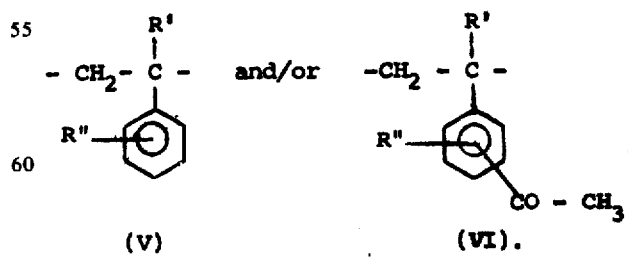

Depending on the process employed, the polyalkenylphenacyl halides can contain halogen atoms attached other than onto the ketone side chain, for example on the aromatic ring.

Likewise, the polyalkenylarylglyoxals can contain an alkenylaromatic part formed exclusively from units:

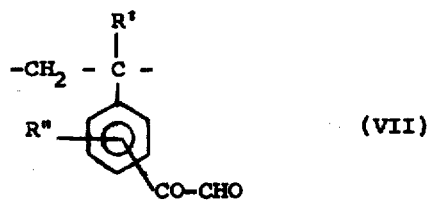

or, simultaneously, from units of formula (VII) and one or more of the units of formulae (IV), (V) and (VI). When the starting polymer is polystyrene, or a polymer in which the para-positions relative to the chain of the aromatic rings are free, the α-ketoaldehyde groups, and likewise the acetyl and halogenoacetyl groups, are principally in the para-position.

The polyalkenylarylglyoxals according to the present invention are of considerable value in extracting nitrogen-containing compounds such as urea and primary or secondary aromatic amines from solutions containing them in water or organic solvents, especially protic solvents such as alcohols. Consequently, the present invention also provides a process for extracting a dissolved nitrogen-containing organic compound which is urea or a primary or secondary for example aromatic amine, which comprises bringing the solution of the nitrogen-containing compound into contact with an alkenylaromatic polymer of the present invention.

Amongst the aromatic amines which can be extracted from their solutions, there may be mentioned especially aniline, toluylamine, chloroanilines and diphenylamine.

The process for extracting nitrogen-containing compounds is especially suitable for isolating such compounds from their aqueous solutions and, in particuular, for treating aqueous effluents containing urea or aromatic amines. More specifically, the present invention relates to the isolation of urea in aqueous solutions resulting from the treatment of blood in artificial kidneys.

It is known that the blood of patients with renal deficiencies is treated either by dialysis or by ultrafiltration in order to remove the waste materials which it contains, especially urea. When dialysis is carried out, the blood circulates in contact with one face of a semipermeable membrane, the other face of which is in contact with an aqueous solution of composition similar to that of blood, which sometimes contains glucose. Before entering the artificial kidney, the dialysis bath generally contains NaCl, MgCl$_2$, CaCl$_2$, KCl, CH$_3$—COONa and, optionally, glucose. On coming out of the dialyser, it contains waste materials originating from the blood, especially urea, which have diffused through the membrane because of the differences in concentration of these waste materials which exist between the blood and the dialysis bath. In order that these compounds are removed as effectively as possible, it is necessary for the concentration difference across the membrane to be kept as large as possible for each compound to be removed, and this implies either replacing the used dialysis bath by a new bath or treating the used bath in order to remove the waste materials completely or partially. A method which is used for lowering the concentration of the used bath consists of introducing it into a storage reservoir of 100 to 300 l of fresh solution in order to dilute it before it is re-used; this procedure rapidly leads, however to the use of large volumes of dialysis liquid. It has also been proposed to remove waste materials by treating the used bath with ion exchange resins or active charcoal, but the efficiency of these processes for isolating nitrogen-containing compounds, more particularly urea, has proved to be poor.

When blood is treated by ultrafiltration, an ultrafiltrate, which contains, in addition to the usual waste materials, water, salts and various low molecular weight solutes, is transferred across a membrane. After removing the waste materials, especially urea, by any suitable means, the resulting ultrafiltrate, the composition of which can be adjusted if necessary, is mixed with the treated blood and the blood thus reconstituted is re-injected into the body of the patient. In this case, the removal of urea and other waste materials from the ultrafiltrate also poses various technical problems which are difficult to solve.

The alkenylaromatic polymers with α-ketoaldehyde groups of the present invention make it possible to remove urea simply and effectively from dialysis baths or from ultrafiltrates resulting from the treatment of blood. In order to extract the dissolved nitrogen-containing compounds, it is sufficient to bring the solutions into contact with the polymers of the invention in any form such as, granules, balls, fibres or membranes. In order to ensure as effective an extraction as possible, it is desirable to have the polymer in a form which provides as large a surface area of contact as possible with the liquid to be treated; finely divided powers, expanded granules or bundles of porous and/or hollow fibres are especially suitable. In the case of aqueous solutions, the medium can be acid, neutral or basic, but it is preferable to carry out the reaction in a pH of between 7 and 12.

The alkenylaromatic polymers with ketoaldehyde groups are also very suitable for extracting organic compounds containing mercaptan groups from their aqueous or organic solutions. Such compounds include aliphatic, cycloaliphatic or aromatic thiols such as methylmercaptan, ethylmercaptan, n-propylmercaptan, i-propylmercaptan, n-pentylmercaptan, 3-pentanethiol, hexylmercaptan, 3-hexanethiol, dodecylmercaptan, n-pentadecanethiol, cyclopentylmercaptan, cyclohexylmercaptan, thiophenol, thiocresols, o-ethylthiophenol, propylthiophenols, and allylthiophenols, which optionally contain hydroxyl, nitro, amino or hydroxycarbonyl groups such as β-mercaptoethanol, 3-hydroxy-propylmercaptan, γ-hydroxybutylmercaptan, β-aminoethylmercaptan, 3-amino-2-propanethiol, 2-N-phenylamino-ethanethiol, ortho-aminothiophenol, thioglycollic acid, α-mercaptopropionic acid, β-mercaptopropionic acid, α-mercaptoisobutyric acid, mercaptovaleric acids, γ-mercaptocaproic acid and mercaptobenzoic acids such as thiosalicylic acid; and mercaptoaminoacids such as cysteine, homocysteine, α-mercapto-γ-aminobutyric acid, β-methylcysteine, β-ethylcysteine, α-aminoγ-methyl-γ-mercaptovaleric acid and β,β-dimethylcysteine. The alkenylaromatic polymers with ketoaldehyde groups are particularly suitable for extracting mercaptoaminoacids from their aqueous solutions; the reaction is preferably carried out on the hydrohalides, especially the hydrochloride.

The polymers of this invention can also be used for binding enzymes, either in order to extract the latter from their aqueous or organic solutions, or to enable them to be used in a supported form in enzymatic reactions.

The polymer can be brought into contact with the solution to be treated in various ways. For example, the polymer can be dispersed in the solution of the compound to be extracted and the whole can be stirred for the period of time necessary for removal of the said compound. The solution can also be passed through a column containing particles of polymers, or it can be forced through membranes comprising bundles of hollow fibres.

The residual groups other than the α-ketoaldehyde groups which may be present in the polymers of this invention by reason of the process by which the polymers were obtained, such as acetyl and haloacetyl groups, do not play any particular role in the process of removing the compounds to be extracted and can be considered to be inert.

The following Examples further illustrate the present invention.

EXAMPLE 1

1. Preparation of poly-p-vinylacetophenone.

500 cm$^3$ of carbon disulphide, 134 g of aluminium chloride and 58.9 g of acetyl chloride are introduced into a 2 l three-neck flask equipped with a stirrer, a dropping funnel, a reflux condenser, a thermometer and a heating device and then a solution of 52 g of polystyrene (molecular weight 1,200) in 500 cm$^3$ of carbon disulphide is introduced over the course of 10 minutes. The contents of the flask are then heated under reflux for 1 hour, after which half of the carbon disulphide is removed by distillation under reduced pressure. 500 cm$^3$ of a normal aqueous solution of hydrochloric acid are then introduced in order to precipitate the polymer, and the remainder of the carbon disulphide is then removed by distillation in vacuo.

The polymer is filtered and washed three times by suspending it in 500 cm$^3$ of a normal aqueous solution of hydrochloric acid. It is then dissolved in 300 cm$^3$ of acetone and then precipitated by introducing the solution obtained into 1,000 cm$^3$ of a normal aqueous solution of hydrochloric acid. This operation is repeated, but carrying out the precipitation in water. The polymer is then washed with water until the chloride ions have disappeared and is then dried at 40°C in vacuo for 24 hours. In this way, 65 g of a polymer which is soluble in acetone, acetic acid and acetic anhydride, and the infra-red spectrum of which corresponds to that of polyvinylacetophenone, are obtained. Its percentage composition is as follows: C = 82.23%, O = 10.36%; and H = 7.10% (theory for a compound containing 1 acetyl group per phenyl group: C = 82.16%, O = 10.945%; and H = 6.895%). This product thus contains approximately 0.915 acetyl group per phenyl ring.

2. Preparation of poly-p-vinylphenacyl bromide.

A solution of 7.3 g of the polyvinylacetophenone obtained above in 160 cm$^3$ of glacial acetic acid is introduced into a 500 cm$^3$ flask equipped with a reflux condenser, a thermometer, a dropping funnel and a stirrer. The temperature of the contents of the flask is lowered to 15°C by immersing it in cold water and then 85.4 cm$^3$ of a 22% by weight per volume solution of hydrobromic acid in acetic acid are added over the course of 10 minutes and, finally, 8 g of bromine are introduced over the course of 4 minutes. After stirring for 10 minutes, a precipitate is formed. Stirring is continued for 3 hours at 15°C.

The polymer is filtered off, washed by suspending it in distilled water until the bromide ions have disappeared and then dried in vacuo at 40°C for 24 hours. In this way, 7.41 g of a product are obtained which has the following percentage composition: C = 55.12%, H = 4.35%, O = 7.60% and Br = 32.97%, which is insoluble in the usual solvents and which swells in dimethylsulphoxide, dimethylacetamide and a 50% by volume mixture of acetone and dioxane. The infra-red spectrum of this polymer has absorption bands at 1,675 and 1,202 cm$^{-1}$ characteristic of the phenacyl bromide group.

The filtrate resulting from the filtration of the insoluble polymer obtained above is introduced into 400 cm$^3$ of distilled water in order to precipitate a polymer which is then filtered off and washed as described above. In this way, 3.02 g of a product are obtained which is insoluble in dimethylsulphoxide, dimethylformamide, acetic acid, 1,2-dichloroethane and chlorobenzene, and the percentage composition of which is as follows: C = 49.96%, H = 4.04%, O = 7.13% and Br = 39.88%. Its infra-red spectrum has absorption bands at 1,675 and 1,202 cm$^{-1}$ characteristic of the phenacyl bromide group.

3. Oxidation of poly-p-vinylphenacyl bromide 0.5 g of soluble polyvinylphenacyl bromide obtained above, dissolved in 10 cm$^3$ of dimethylsulphoxide, is introduced into a 25 cm$^3$ conical glass flask equipped with a magnetic stirrer and heated on a water bath kept at 37°C. The solution is kept at 37°C for 15 hours. The solution is then introduced into a mixture of 50 g of ice and 50 g of water in order to precipitate the polymer which is then filtered off and washed with water until the bromide ions have disappeared and then dried. In this way, 0.35 g of a product are obtained which is soluble in acetone, dimethylsulphoxide, dimethylformamide and dioxane and the percentage composition of which is as follows: C = 61.34%, H = 4.93%, O = 17.79% and Br = 15.94%. The infra-red spectrum of this polymer has an absorption band at 3,390 cm$^{-1}$ characteristic of —C—OH groups which can be attributed to the hydrated form of the aldehyde group or to a —CH$_2$ —OH group in the α-position to the acetone group. A significant disappearance of the bands at 1,675 and 1,202 cm$^{-1}$ corresponding to the phenacyl bromide group is also noted on the infra-red spectrum.

The presence of a —CO—CHO group in the product obtained is confirmed in the following way:

a. A sample of the polymer dissolved in dimethylsulphoxide is reacted with 2,4-dinitro-phenylhydrazine dissolved in ethanol, in the presence of concentrated hydrochloric acid at 37°C for 30 minutes. A precipitate is obtained which is washed and then dried to constant weight.

The ultraviolet spectrum of a solution in chloroform gives a maximum at 25,700 cm$^{-1}$ (with a shoulder in the visible at about 18,200 cm$^{-1}$). The visible spectrum of alkaline solutions in 1% sodium hydroxide shows a maximum at 18,900 cm$^{-1}$; the colouration is stable for 2 hours. These characteristics are those of an osazone derived from a carbonyl bonded to a phenyl group of an aldehyde group in the α-position to this carbonyl.

b. The —CO—CHO groups are determined by converting the phenylglyoxal groups to mandelic acid groups by a known excess of sodium hydroxide [c.f. A KJAER, Acta Chem. Scand., 4, 892-900 (1950); and H. J. Fischer et al., J. Am. Chem. Soc., 94, 1434 – 6 (1942)]. The sodium hydroxide which was not consumed is then determined by acidimetry in a back titration using hydrochloric acid. The following procedure is carried out:

100 mg of polymer, 3 cm$^3$ of dimethylsulphoxide and 2.5 cm$^3$ of a 0.5 N sodium hydroxide solution are stirred for 15 minutes at ambient temperature and then 10 cm$^3$ of distilled water are added and the sodium hydroxide which has not reacted is measured using 0.05 N HCl. No trace of bromide ions, which could result from the saponification of the residual bromine present in the polymer, is observed.

A direct determination using 0.1 N sodium hydroxide solution shows that the polymer does not contain any acid group and consequently that all the sodium hydroxide was used to convert the phenylglyoxal groups to mandelic acid groups in accordance with the equation:

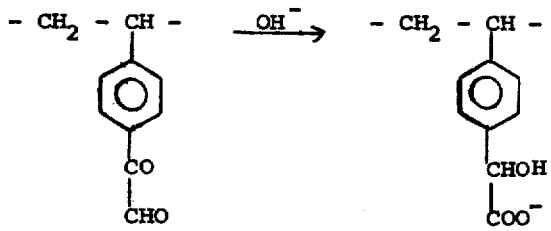

In this way, it is found that the polymer obtained contains 0.36 equivalent of a —CO—CHO group per 100 g, corresponding to 0.72 —CO—CHO group per phenyl group.

EXAMPLE 2

1. Preparation of poly-p-vinylacetophenone.

The procedure of Example 1 is followed, but starting from 85.28 g of a polystyrene of molecular weight 3,000. In this way, 106 g of polymer are obtained which is soluble in acetone, acetic acid and acetic anhydride and the percentage composition of which is as follows: C = 82.33%, H = 6.95% and O = 10.71%. The infra-red spectrum of this polymer corresponds to that of poly-p-vinylacetophenone.

The polymer obtained contains 0.934 acetyl group per phenyl ring.

2. Bromination of poly-p-vinylacetophenone.

The procedure of Example 1 is followed, starting from 36.5 g of the poly-p-vinylacetophenone obtained above. In this way, the following are obtained:

a. 50 g of a polymer which precipitates during the reaction and the percentage composition of which is as follows: C = 54.26%, H = 4.45%, O = 7.82% and Br = 33.47% and the infra-red spectra of which show bands characteristic of p-vinylacetophenone and p-vinylphenacyl bromide units.

b. 2.5 g of a polymer reprecipitated from the reaction medium as in Example 1.

3. Oxidation of poly-p-vinylphenacyl bromide.

The reaction is carried out as in Example 1, but at 50°C, by introducing 22.5 g of the insoluble polymer obtained above and 500 cm$^3$ of dimethylsulphoxide. After 15 hours' reaction, a product is filtered off and washed with water until the bromide ions have disappeared and then dried. In this way, 19 g of a product are obtained which is insoluble in the usual organic solvents and the percentage composition of which is as follows: C = 65.86%, H = 5.56%, O = 17.66% and Br = 10.91%, and in which 0.36 equivalent of a phenylglyoxal group per 100 g of polymer are present, corresponding to 0.68 equivalent per phenyl ring (measured as in Example 1).

EXAMPLE 3

1. Preparation of a crosslinked poly-p-vinylacetophenone.

A crosslinked poly-p-vinylacetophenone is prepared by acetylating a copolymer obtained by polymerising 150 g of styrene and 1.5 g of p-divinylbenzene in water in the presence of 0.3 g of polyvinyl aclohol and 0.75 g of benzoyl peroxide, by carrying out the following procedure:

100 cm$^3$ of nitrobenzene are introduced into a 250 cm$^3$ flask equipped with a stirrer, a reflux condenser, a thermometer and an oil bath heating system and then 13.35 g of aluminium chloride are introduced with stirring; after the latter has dissolved, 5.89 g of acetyl chloride and 5.20 g of a styrene/divinylbenzene copolymer are added. The temperature of the contents of the flask is raised to 55° – 60°C and these conditions are maintained for 17 hours. The reaction mixture is then cooled and the polymer is filtered off and then treated with 125 cm$^3$ of a normal solution of hydrochloric acid in methanol until the chloride ions have disappeared; it is then dried in vacuo at 40°C.

In this way, 6.81 g of a product are obtained, the percentage composition of which is as follows: C = 83.70%, H = 6.99% and O = 9.30%. The infra-red spectrum of this polymer shows bands characteristic of p-vinylacetophenone units. This polymer contains 0.77 acetyl group per phenyl ring.

2. Preparation of a crosslinked poly-p-vinylphenacyl bromide.

The procedure of Example 1 is followed for brominating the non-crosslinked poly-p-vinylacetophenone, by introducing 1.46 g of the polymer obtained above. In this way, 2 g of an insoluble polymer are obtained, the percentage composition of which is as follows: C = 63.97%, H = 5.64%, O = 7.91% and Br = 22.77%. The infra-red spectrum of the polymer shows absorption bands at 1,680 and 1,364 cm$^{-1}$ and at 1,202 cm$^{-1}$ characteristic of p-vinylacetophenone and p-vinylphenacyl bromide units.

3. Preparation of a crosslinked polystyrylglyoxal.

1.5 g of the polymer obtained above are oxidised, in accordance with the procedure described in Example 1, by 50 g of dimethylsulphoxide at 90°C. In this way, 1.1 g of a product are obtained, the percentage composition of which is as follows: C = 75.39%, H = 6.19%, O = 15.79% and Br = 2.62%. The infra-red spectrum of this polymer indicates a significant disappearance of the p-vinylphenacyl bromide groups and the presence of -C-OH groups characterised by a band at 3,390 cm$^{-1}$ which can be attributed to the hydrated form of the aldehyde group of the —CO—CHO group, this group being determined as in Example 1 by converting the phenylglyoxal radical into a mandelic acid radical by reacting it with sodium hydroxide for 2 hours 30 minutes. The polymer contains 0.187 —CO—CHO group per 100 g, corresponding to 0.31 group per phenyl ring.

EXAMPLE 4

1. Preparation of a crosslinked poly-p-vinylphenacyl chloride.

1,500 cm$^3$ of nitrobenzene are introduced into a 3 l flask equipped with a reflux condenser, a thermometer and an oil bath heating system and then 267 g of aluminium chloride are introduced in 3 portions, with stirring; after the latter has dissolved, 169.5 g of acetyl chloride and 104 g of a crosslinked styrene/p-divinylbenzene copolymer, such as that obtained in the preceding Example, are added. The contents of the flask are heated to 50°C. The reaction mixture is kept under these conditions for 3 hours and then cooled to ambient temperature and introduced into 1,500 cm$^3$ of a normal solution of hydrochloric acid in acetone; the mixture is stirred for 2 hours and then the polymer is filtered off. It is then washed 4 times in 2 l of the same hydrochloric acid solution and then with acetone until the chloride ions have disappeared. After drying in vacuo at 40°C for 24 hours, 165.5 g of a polymer are obtained, the percentage composition of which is as follows: C = 67.95%, H = 5.47%, O = 8.36% and Cl = 17.86%. The infra-red spectrum of this polymer shows absorption bands at 1,675 cm$^{-1}$ and 1,212 cm$^{-1}$, characteristic of phenacyl chloride groups.

2. Preparation of crosslinked polystyreneglyoxal.

4.5 g of poly-p-vinylphenacyl chloride obtained above in 50 cm$^3$ of dimethylsulphoxide are heated at 100°C for 15 hours. The polymer is then treated as in Example 3. 4.20 g of a polymer of the following percentage composition are obtained. C = 74.87%, H = 5.75%, O = 17.56% and Cl = 1.81% and in which 0.26 -CO-CHO group per 100 g are detected by means of sodium hydroxide in accordance with the method described in Example 1. This polymer contains 0.43 ketoaldehyde group per phenyl ring.

EXAMPLE 5

25 mg of polystyrylglyoxal prepared in Example 1, 5 cm$^3$ of an aqueous solution of urea of concentration 1 mol/1 and 5 cm$^3$ of a solution containing 0.05 mol of monopotassium phosphate per litre, brought to pH 7 by adding sodium hydroxide, are introduced into a 100 cm$^3$ conical glass flask. The contents of the flask are then stirred for 15 hours at 37°C. The contents of the apparatus are cooled and the polymer is filtered off, washed 10 times in 20 cm$^3$ of water and then dried in vacuo. A product is obtained in which 2.40% of nitrogen are measured by the Dumas method. 51.5 g of urea have thus been attached per kg of polymer.

EXAMPLE 6

The procedure of Example 5 is followed, but introducing 5 cm$^3$ of a solution containing 0.05 mol/1 of sodium carbonate and bicarbonate. The pH of the solution is 10. Under these conditions the weight of urea attached is 61.5 g/kg of polymer.

EXAMPLES 7 to 10

The procedure of Example 5 is followed, using various polystyrylglyoxals, the characteristics of which and the method for producing them are given in the following table which also contains the results obtained:

| EX. | Polystyrylglyoxal No. of —CO—CHO equivalents/ phenyl ring | Obtained in Example | pH of the urea solution | Nitrogen measured in % by weight of polymer | Urea Attached in g/kg of polymer |
|---|---|---|---|---|---|
| 7 | 0.72 | 2 | 7 | 1.46 | 31.3 |
| 8 | " | " | 10 | 2.07 | 44.3 |
| 9 | 0.68 | 3 | 7 | 0.80 | 17.15 |
| 10 | " | " | 10 | 1.40 | 30 |

EXAMPLES 11 to 15

The procedure of Example 5 is followed, using 200 mg of polymer and 30 cm$^3$ of an aqueous solution of urea of concentration 1 g/l.

The results obtained are given in the following table:

| EX. | Polystyrylglyoxal —COCHO equivalents/ phenyl ring | Polymer prepared according to Example | pH | Contact time | Nitrogen measured % by weight/ polymer | Urea attached g/kg of polymer |
|---|---|---|---|---|---|---|
| 11 | 0.72 | 2 | 7 | 2 hrs. 30 mins. | 0.18 | 3.85 |
| 12 | " | " | 7 | 15 hrs. | 0.22 | 4.70 |
| 13 | " | " | 10 | 2 hrs. 30 mins. | 0.40 | 8.25 |
| 14 | " | " | 10 | 15 hrs. | 0.885 | 18.5 |
| 15 | 0.68 | 3 | 10 | 15 hrs. | 0.35 | 7.5 |

EXAMPLE 16

The procedure of Example 5 is followed, introducing 0.5 g of polystyrylglyoxal prepared in Example 2, 10 cm³ of an aqueous solution containing 0.35 mol of aniline per litre and 10 cm³ of an aqueous solution containing 0.05 mol of monopotassium phosphate per litre, brought to pH 7 by adding sodium hydroxide, into the conical flask. The mixture is stirred for 15 hours at 37°C and then the polymer is treated as in Example 5. 0.591 g of product is recovered, in which 2.16% by weight of nitrogen are measured, which corresponds to 140 g of aniline having been attached per kg of polymer.

EXAMPLE 17

0.325 g of a polymer prepared as in Example 1 and containing 0.004 -CO-CHO group per gram, followed by 20 cm³ of an M/10 aqueous solution of cysteine hydrochloride are introduced into the apparatus of Example 5. The residual acid is determined by acidimetry; after stirring for 15 hours, it is found that 2.7 milliequivalents of cysteine have been attached per gram of polymer (corresponding to 0.0009 mol of the 0.002 mol employed).

We claim:
1. An alkenylaromatic polymer consisting essentially of:
   a. 50–100% of recurring units of the formula:

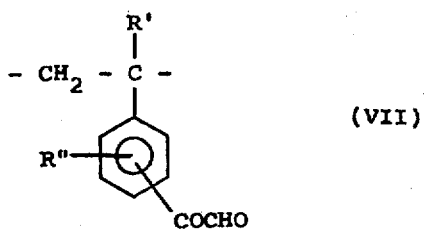

or recurring units of formula (VII) and recurring units selected from units of the formula:

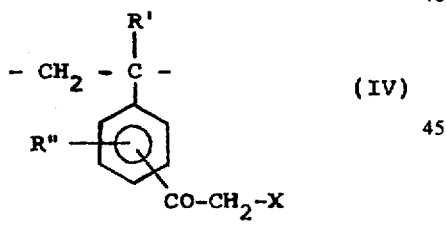

and

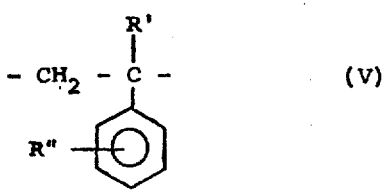

and

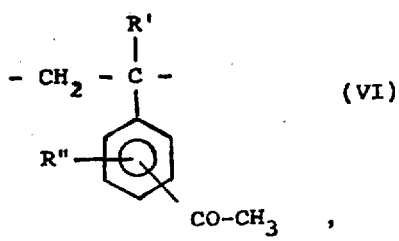

at least 0.01% of the recurring units being recurring units of formula (VII); and
   b. 0–50% of recurring units of a non-aromatic ethylenically unsaturated monomer,
   in which R' represents a hydrogen atom or a methyl radical, R" represents a hydrogen atom or a methyl or ethyl radical and X represents a halogen atom;
   at least one of the aromatic rings in the recurring units of formulae (VII), (IV), (V), and (VI) optionally being substituted by halogen.

2. A polymer according to claim 1 which is cross-linked by units of a polyvinyl monomer, said units being present in an amount from 0.1 to 30% based on the total number of units of formulae (VII), (IV), (V) and (VI).

3. A polymer according to claim 1 in which R" represents a hydrogen atom.

4. A polymer according to claim 1, in which the non-aromatic ethylenically unsaturated monomer is ethylene, propylene, butadiene or isoprene.

5. A polymer according to claim 2, in which the polyvinyl monomer is m-divinylbenzene, p-divinylbenzene, diisopropenylbenzene, a divinyltoluene, 1,3,5,-trivinylbenzene, 1,2,4-trivinylbenzene or a divinylxylene.

6. A polymer according to claim 2 in which R" represents a hydrogen atom.

7. A polymer according to claim 5 in which the polyvinyl monomer is divinylbenzene and R' and R" both represent a hydrogen atom.

8. Process for the preparation of an alkenylaromatic polymer as defined in claim 1, which comprises reacting dimethylsulphoxide with an alkenylaromatic polymer consisting essentially of:
   a. 50–100% of recurring units of the formula:

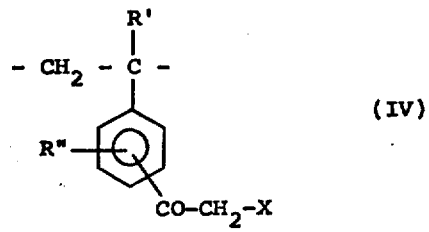

or recurring units of formula (IV) and recurring units selected from units of the formula:

b. 0-50% of recurring units of a non-aromatic ethylenically unsaturated monomer.

9. Process according to claim 8, in which the reaction is carried out at a temperature between 0° and 200°C.

10. Process according to claim 9, in which the reaction is carried out at a temperature of between 20° and 150°C.

11. Process according to claim 8, in which dimethylsulphoxide is used as the reaction medium.

12. Process according to claim 8 in which the polymer is cross-linked by units of a polyvinyl monomer, said units being present in an amount from 0.1 to 30% based on the total number of units of formulae (IV), (V) and (VI).

13. Process according to claim 8 in which R'' represents a hydrogen atom.

14. Process according to claim 12 in which R'' represents a hydrogen atom.

15. Process according to claim 12 in which the polyvinyl monomer is divinylbenzene and R' and R'' both represent a hydrogen atom.

16. A polymer according to claim 2 consisting essentially of 100% of recurring units (a).

17. A polymer according to claim 2 consisting essentially of 100% of recurring units (a) and X represents a bromine atom.

18. Process according to claim 12 in which the polymer consists essentially of 100% of recurring units (a) and X represents a bromine atom.

* * * * *